US008608907B2

(12) United States Patent
Hunke et al.

(10) Patent No.: US 8,608,907 B2
(45) Date of Patent: Dec. 17, 2013

(54) FLUORESCENT WHITENING AGENT COMPOSITIONS

(75) Inventors: Bernhard Hunke, Hennef (DE); Michael Kraemer, Kürten (DE); Andrei Tauber, Köln (DE); Günter Klug, Langenfeld (DE)

(73) Assignee: Blankophor GmbH & Co. KG (DE)

( * ) Notice: Subject to any disclaimer, the term of this patent is extended or adjusted under 35 U.S.C. 154(b) by 188 days.

(21) Appl. No.: 12/997,046

(22) PCT Filed: Jun. 10, 2009

(86) PCT No.: PCT/EP2009/057198
§ 371 (c)(1),
(2), (4) Date: Jan. 14, 2011

(87) PCT Pub. No.: WO2009/150182
PCT Pub. Date: Dec. 17, 2009

(65) Prior Publication Data
US 2011/0094694 A1   Apr. 28, 2011

(30) Foreign Application Priority Data

Jun. 11, 2008   (EP) .................................. 080105927

(51) Int. Cl.
*D21H 17/07* (2006.01)
*D21H 17/09* (2006.01)
*D21H 21/30* (2006.01)
*D21H 23/04* (2006.01)
*D21H 23/22* (2006.01)
*C07D 403/00* (2006.01)
*C07D 403/12* (2006.01)
*C09K 11/06* (2006.01)

(52) U.S. Cl.
USPC . 162/162; 162/158; 252/301.21; 252/301.23; 544/193.2; 544/198; 8/648

(58) Field of Classification Search
USPC ................................. 162/158, 162, 183–185; 252/301.21–23; 544/193–194, 198, 544/204, 210; 8/648
See application file for complete search history.

(56) References Cited

U.S. PATENT DOCUMENTS 3,272,805 A   9/1966 Hausermann et al.
3,682,907 A * 8/1972 Ohkawa et al. ............... 544/83
(Continued)

FOREIGN PATENT DOCUMENTS

EP   08010592.7   6/2009
GB   1010759      11/1965
(Continued)

OTHER PUBLICATIONS

International Search Report and Written Opinion for PCT Application No. PCT/EP2009/057198; International Filing Date: Jun. 10, 2009; Date of Mailing: Aug. 26, 2009; 9 pages.
(Continued)

*Primary Examiner* — Yogendra Gupta
*Assistant Examiner* — Dennis Cordray
(74) *Attorney, Agent, or Firm* — Cantor Colburn LLP (57) ABSTRACT

A composition suitable for paper brightening, wherein the composition contains one or more specified fluorescent whitening agents with taurine groups. The composition is used for whitening paper, in particular at the wet-end, in the size press or by coating.

13 Claims, 2 Drawing Sheets

(56) References Cited

U.S. PATENT DOCUMENTS

| | | | |
|---|---|---|---|
| 4,466,900 A | 8/1984 | Horlacher et al. | |
| 6,207,258 B1* | 3/2001 | Varnell | 428/32.1 |
| 6,365,737 B1* | 4/2002 | Metzger et al. | 544/193.2 |
| 6,746,832 B2* | 6/2004 | Okazaki et al. | 430/363 |
| 6,919,452 B1* | 7/2005 | Kimura et al. | 544/193.2 |
| 2003/0089888 A1* | 5/2003 | Bacher et al. | 252/301.21 |
| 2006/0252872 A1 | 11/2006 | Jonckheree | |

FOREIGN PATENT DOCUMENTS

| | | |
|---|---|---|
| GB | 1021527 | 3/1966 |
| JP | 06-332127 A1 | 7/1996 |
| JP | 08-184939 A1 | 7/1996 |
| WO | 9600220 | 1/1996 |
| WO | 9842685 A1 | 10/1998 |
| WO | 0055688 A1 | 9/2000 |
| WO | 03044275 | 5/2003 |
| WO | 2004005617 | 1/2004 |
| WO | 2005068597 | 7/2005 |
| WO | 2007048720 | 5/2007 |
| WO | 2009150182 A1 | 12/2009 |

OTHER PUBLICATIONS

International Preliminary Report on Patentability for International Application No. PCT/EP2009/057198; filed: Jun. 10, 2009; report issued on Dec. 14, 2010; 6 pages.

* cited by examiner

Fig. 2

FLUORESCENT WHITENING AGENT COMPOSITIONS

CROSS REFERENCE TO RELATED APPLICATIONS

This is a U.S. national stage of application No. PCT/EP2009/057198, filed on 10 Jun. 2009. Priority under 35 U.S.C. §119(a) and 35 U.S.C. §365(b) is claimed from European Application No. 08010592.7, filed 11 Jun. 2008, the disclosure of which is also incorporated herein by reference.

BACKGROUND

The present invention relates to fluorescent whitening agent compositions comprising specific bis-triazinylamino-stilbene compounds containing taurine groups for whitening paper.

In the paper-producing industry there is a continuing trend towards papers having high whiteness. Whitening paper is usually carried out by using a fluorescent whitening agent (FWA) either before the sheet formation in the paper pulp or after sheet formation, in the size press or by coating compositions. A combination of more than one of said processes is also possible.

BRIEF SUMMARY

Surprisingly, it has been found that specific bis-triazinylamino-stilbene compounds containing taurine groups when used for whitening paper yield paper of improved whiteness. In particular this also applies when said compounds are used in combination with inorganic salts of bivalent cations, e.g. calcium chloride. Such salts are used for improving printing performance, especially of inkjet printings, in the paper production industry.

Therefore, the present invention relates to a composition suitable for paper brightening, wherein the composition contains at least one fluorescent whitening agent (FWA) of the formula (1), the formula (2) or the formula (3)

wherein

R represents independently hydrogen, $C_1$-$C_3$ alkyl or $C_1$-$C_3$ hydroxyalkyl;

$R_1$, $R_2$, $R_3$ and $R_4$ represent independently of each other, hydrogen, cyano, $C_1$-$C_4$ alkyl, $C_2$-$C_4$ hydroxyalkyl, $C_1$-$C_4$ alkoxy, wherein alkyl is linear or branched; or $R_2$ and $R_1$ or $R_3$ and $R_4$ independently of each other together with N atom form morpholine, piperidine or pyrrolidine ring; or —$(CH_2)_l$—$SO_3M$, where l is 1, 2 or 3; or wherein the —$SO_3M$ groups can be in o-, m-, or p-position and k is an integer from 0 to 3, preferably from 1 to 3; or —$(CH_2)_i$—COOR, —$(CH_2)_i$—CONHR, —$(CH_2)_i$—COR, where i is an integer from 1 to 4, R is $C_1$-$C_3$ alkyl or equals to M; and M represents hydrogen, or one equivalent of a cation, in particular Li, Na, K, Ca, Mg, ammonium, or ammonium which is mono- di-, tri- or tetra-substituted by $C_1$-$C_4$ alkyl or $C_2$-$C_4$ hydroxyalkyl;

with the proviso that, in case that the fluorescent whitening agent of the formula (1) is present and that none of the fluorescent whitening agents of the formulae (2) and (3) is present, R is not hydrogen or methyl.

The invention further relates to a process for whitening paper, wherein a pulp and/or a cellulose sheet is brought into contact with the above defined composition. Further, the invention refers to paper obtainable by this process. In addition, the invention relates to the use of the above defined composition for whitening paper. Preferred embodiments of the invention are described in the description (including the examples) hereinafter, the claims and the figures.

DETAILED DESCRIPTION

In a preferred embodiment of the invention, the composition suitable for paper brightening is a size press liquor, and the process is a process for whitening paper in the size press, wherein a cellulose sheet is brought into contact with the size press liquor.

In the context of this invention, size press is understood as meaning a surface application unit, preferably of the paper machine, in which the cellulose sheet formed is brought into contact with a size press liquor, and in which the proportion of the liquor which is to be taken up by the sheet (liquor absorption) can preferably be adjusted by means of the roll pressure.

Recent developments of the size press or film press, namely of the Speedsizer as well as of the Symsizer as well Gate-roll, are likewise understood as being covered by the term size press.

In another preferred embodiment of the invention, the composition suitable for paper brightening is a coating composition or coating slip, and the process is a process for whitening paper, wherein a cellulose sheet is brought into contact with the coating composition or coating slip.

In another preferred embodiment of the invention, the composition suitable for paper brightening is a wet-end composition, and the process is a process for whitening paper, wherein a pulp or pulp suspension is brought into contact with the said composition.

According to the invention the composition contains at least one bis-triazinylamino-stilbene compound of the above defined formula (1), (2) or (3). In a preferred embodiment, R, R1 and R3 are hydrogen, and R2 and R4 are both 2,5-disulfophenyl. In another preferred embodiment, R is methyl, R1 and R3 are hydrogen, and R2 and R4 are both 2,5-disulfophenyl.

Preferred embodiments of M are hydrogen, Na, K, Ca, Mg, in particular M is Na or K, most preferred is Na.

The fluorescent whitening agents of formula (1), formula (2) and formula (3) can be produced analogously to methods known in the art. For example, the fluorescent whitening agents can be prepared by reacting cyanuric chloride with an amine or aniline compound or derivative, 4,4'-diaminostilbene-2,2'-disulfonic acid or a salt thereof, and a taurine compound or taurine/ditaurine compounds mixture. Alternatively, the compounds of formula (1), formula (2) and formula (3) could be also prepared separately by methods known in the art and mixed together after the preparation. Suitable processes are described in the examples below. Fluorescent whitening agents of formula (1), wherein R is hydrogen or methyl, are known from Examples of WO 03/044275 A1.

The composition of the invention can contain two or three fluorescent whitening agents of the formula (1), formula (2) or formula (3). Generally, the composition of the invention can comprise one of the following embodiments:

fluorescent whitening agent of formula (1) with the proviso as defined above;
fluorescent whitening agent of formula (2);
fluorescent whitening agent of formula (3);
fluorescent whitening agents of formulae (1) and (2);
fluorescent whitening agents of formulae (1) and (3);
fluorescent whitening agents of formulae (2) and (3); or
fluorescent whitening agents of formulae (1), (2) and (3).

Most preferably, the composition contains the fluorescent whitening agents of the formulae (1), (2) and (3). The composition can contain one or more of each of a fluorescent whitening agent of the formulae (1), (2) and/or (3). In addition, the composition can contain one or more known bis-triazyinylamino-stilbene or distyryl-biphenyl based fluorescent whitening agents.

The composition of the invention contains preferably the fluorescent whitening agent of formula (1) in an amount of 0 to 99 weight-%, preferably 20 to 95 weight-%, most preferably 50 to 95 weight-%; the fluorescent whitening agent of formula (2) in an amount of 0 to 90 weight-%, preferably 0.1 to 60 weight-%, most preferably 1 to 30 weight-%; and the fluorescent whitening agent of formula (3) in an amount of 0.1 to 50 weight-%, preferably 0.1 to 30 weight-%, most preferably 0.1 to 20 weight-%; in each case based on 100 weight-% of the component (a). In another preferred embodiment of the invention the composition contains the fluorescent whitening agent of formula (1) in an amount of 0 to 99 weight-%, the fluorescent whitening agent of formula (2) in an amount of 0 to 90 weight-%, and the fluorescent whitening agent of formula (3) in an amount of 0 to 50 weight-%, in each case based on 100 weight-% of the component (a).

The composition of the invention may be used in any commercially available form, e.g. as powders or granules, which may be dissolved in water, or it may be used in the form of an aqueous preparation, an aqueous solution, or an aqueous dispersion, or an aqueous preparation directly from the production. In a preferred embodiment, the composition is an aqueous preparation. In a further preferred embodiment, the composition of the invention contains as component (b) water, preferably in an amount of 40 to 99 weight-%, preferably 60 to 97 weight-%, most preferably 70 to 95 weight-%, in each case based on 100 weight-% composition.

Depending on its use, the composition of the invention can contain carriers, sizing agents, a salt of a bivalent cation, and in addition, in relatively small amounts, usually in amounts of less than 10% by weight, further auxiliaries, such as, for example, dispersants, thickeners, antifreezes, preservatives, complexing agents, etc., or organic byproducts from the fluorescent whitening agent synthesis which were not completely removed in the working-up, may be contained in the composition of the invention. In a preferred embodiment of the invention the composition is a size press liquor containing the fluorescent whitening agent as defined above (component (a)), water (component (b)), and at least one carrier and/or sizing agent. In another preferred embodiment of the invention the composition is a coating composition or coating slip containing the fluorescent whitening agent as defined above (component (a)), water (component (b)), at least one binder and/or pigment and, optionally, at least one carrier and/or co-binder.

Suitable carriers are any compounds known in the art to be suitable as carrier, in particular carriers suitable for size press liquors or coating compositions. Preferred carriers are carboxymethylcellulose (CMC), polyvinyl alcohol (PVA), starch or mixtures thereof, with starch being particularly preferred. Suitable carrier substances are, for example, hydrophilic polymers having the ability to form hydrogen bridge bonds. Preferred carrier substances are starch, polyvinyl alcohols, carboxymethylcelluloses and polyethylene glycols having a number average molecular weight of from 200 to 8000 g/mol, as well as any desired mixtures of these substances, it being possible for these polymers optionally to be modified. Preferred polyvinyl alcohols are those having a degree of hydrolysis >85%, preferred carboxymethylcelluloses are those having a degree of substitution DS of >0.5. Polyethylene glycols having a number average molecular weight Mn of from 200 to 8000 g/mol are particularly preferred. Suitable starches are based e.g., but not exclusively, on potato starch, rice starch, wheat starch, maize starch or tapioca starch. In particular, starches whose molecular weights have already been reduced by partial degradation and/or which have been obtained by derivatization are preferably used instead of natural starches. Furthermore, starches for which both modification steps have been combined, i.e. which have been partially degraded and additionally derivatized, are suitable. Typical methods for starch degradation are, for example, enzymatic, oxidative, thermal or hydrolytic treatment. Examples of suitable starch derivatives are hydroxyethyl starch or cationic starch.

Suitable sizing agents are alkenyl ketene dimers, alkyl ketene dimer (AKD), alkenyl succinic anhydride (ASA), rosin size, styrene maleic anhydride copolymers, styrene acrylate, styrene acrylic acid copolymers, polyurethane or ethylene acrylic acid copolymers, or other common paper chemicals, such as styryl-acrylate copolymers, latex, pigments, defoamers, or salts, such as NaCl or NaHCO3, or mixtures of two or more thereof. If sizing agents are used, they are used in amounts of 0 to 5, in particular 0 to 4, most preferably 0 to 3, in each case weight-% based on 100 weight-% of the composition.

The coating slips or coating compositions to be brightened according to the invention contain, as latex binder, for example lattices based on styrene/butadiene, styrene/acrylate or vinyl acetate. These polymers can optionally be modified by further monomers, such as acrylonitrile, acrylamide, $\alpha,\beta$-unsaturated carboxylic acids, such as acrylic acid, methacrylic acid, itaconic acid or maleic acid, acrylates, vinyl esters, ethylene, vinyl chloride, vinylidene chloride, etc. In general, however, all customary latex binders which are used for the preparation of paper coating slips or coating compositions are suitable. The coating slips or coating compositions can contain as synthetic co-binders differing from these, for example, carboxymethylcellulose, hydroxylalkylcellulose and/or polyvinyl alcohol and acrylate-based synthetic thickeners.

Preferred latex binders are those based on styrene/butadiene. Preferred synthetic co-binders are polyvinyl alcohols, in particular those having a degree of hydrolysis of >85%, and in particular a Brookfield viscosity of 2-80 mPas (measured on a 4% strength aqueous solution at 20° C.), carboxymethylcelluloses, in particular those having a degree of substitution of >0.5, and in particular a Brookfield viscosity of from about 5 to about 5000 mPas (measured on a 2% strength aqueous solution at 20° C.) and mixtures of these two substances.

The coating slips or coating compositions to be brightened according to the invention preferably furthermore contain white pigments.

Customarily used white pigments are calcium carbonate in natural or precipitated form, kaolin, talc, titanium dioxide, satin white, aluminum hydroxide and barium sulfate, often also in the form of mixture.

Suitable salts of a bivalent cation comprise bivalent cations, preferably cations of an earth alkaline metal, in particular calcium or magnesium. Preferably, the counterions of the bivalent cations are mono- or multivalent anions, in particular halide, sulphate, hydrosulphate, phosphate, hydrophosphate, dihydrophosphate, carbonate, hydrocarbonate, nitrate, acetate, or a mixture thereof, preferably chloride or sulphate, most preferably chloride. A preferred salt is calcium chloride, magnesium chloride, magnesium sulphate, or a mixture thereof; more preferred is calcium chloride, magnesium chloride, or a mixture thereof; most preferred is calcium chloride.

The production of the composition may be effected by known methods and preferably effected by combining an aqueous solution of the fluorescent whitening agent used as component (a), which preferably has a suitable pH value, with the other components, such as carrier substances, sizing agents, binders, pigments, salts or standardizing agents.

The process of the invention for whitening paper is carried out according to known processes, preferably using a size press or coating, and is subject to no restrictions. The paper used is not critical and may be any pulp or cellulose sheet.

Paper obtained by the process of the invention exhibits improved whiteness, and, in case that a salt of a bivalent cation is used, is in particular suitable for inkjet printing applications.

The whiteness of the papers produced can be characterized by the CIE whiteness. Different fluorescent whitening agents can be compared to each other with respect to the saturation behavior when determined according to CIE whiteness. In other words, if a larger amount of fluorescent whitening agent is used and no further increase in whiteness is found, there is a saturation behavior and there may even be adverse effects on the whiteness when using higher amounts. The effect of saturation is also referred to as greening. The greening limit, i.e. the point at which increasing amounts of fluorescent whitening agent used results in virtually no further increase in whiteness, can be derived, for example, from the a*-b* diagram, where a* and b* are the color coordinates in the CIE-L*a*b system.

The invention also relates to the use of the composition of the invention for whitening paper, wherein there is used a composition as defined above.

The following examples illustrate the invention and show preferred embodiments, without limiting the scope of protection.

EXAMPLES

Example 1

Step 1: Reaction of Cyanuric Chloride With Dimetanilic Acid

A two-liter flask equipped with an agitator, pH electrode, thermometer and condenser is charged with 600 ml of water at 8° C., and 100 g (0.54 mol) of cyanuric chloride. After pH is decreased to 4.5, 592 g (0.56 mol) of a 25% w/w dimetanilic acid solution is added in 45 minutes. The pH is maintained at 2.3 by the simultaneous addition of 10% sodium hydroxide solution while heating the mixture up to 12° C. After the addition of dimetanilic acid solution the mixture is stirred for 3 hours at 12° C. and pH 2.3. After this time the temperature is increased to 30° C. and the reaction is completed while the pH is maintained at 5.2 by addition of 10% sodium hydroxide solution.

Step 2: Reaction of the Step 1 Intermediate With 4,4'-diamino-2,2'-disulfonic acid A solution containing 112.2 g (0.27 mol) of 4,4'-diamino-2,2'-disulfonic acid disodium salt, 835 g of water and 222 g of 10% water solution of sodium carbonate are added to the solution from step 1. The pH of the solution was kept constant during the addition (pH=5.2) while temperature was gradually increased up to 65° C. The solution is stirred at 65° C. and pH 5.2 until the addition of the 4,4'-diamino-2,2'-disulfonic acid solution is finished.

Step 3: Reaction of the Step 2 Intermediate With Taurine (1), (R, R1, R3=H; R2, R4=C6H3(SO3Na)2)

67.8 g (0.54 mol) of taurine as 20% water solution are added to the solution from step 2 during 20 minutes. The pH is kept constant at 8 by the simultaneous addition of 10% sodium hydroxide solution while heating the mixture up to 100° C. The reaction mixture is then stirred at about 100° C. and pH 8 for additional 3 hours. The resulting solution is cooled to about 50° C. and clarified by filtration to yield the solution of the compound of formula 1, 371 g (87.3%).

Example 2

(R, $R_1$, R3=H; R2, R4=C6H3(SO3Na)2)

67.8 g (0.54 mol) of taurine/ditaurine mixture (5/1 w/w) as 20% water solution are added to the solution from step 2 of Example 1 during 20 minutes. The pH is kept constant at 8 by the simultaneous addition of 10% sodium hydroxide solution while heating the mixture up to 100° C. The reaction mixture is then stirred at about 100° C. and pH 8 for additional 3 hours. The resulting solution is cooled to about 50° C. and clarified by filtration to yield the solution of mixture of 1 (78.7%), 2 (4.8%) and 3 (16.5%) in overall yield of 362 g (85.2%).

Example 3

(R, R1, R3=H; R2, R4=C6H3(SO3Na)2)

Solution from the step 2 of Example 1 was heated up to 60° C., then 67.8 g (0.54 mol) of taurine/ditaurine mixture (5/1 w/w) as 20% water solution were added dropwise in 1 hour. The pH is kept constant at 8 by the simultaneous addition of 10% sodium hydroxide solution while heating the mixture up to 100° C. The reaction mixture is then stirred at about 100° C. and pH 8 for additional 3 hours. The resulting solution is cooled to about 50° C. and clarified by filtration to yield the solution of mixture of 1 (84%), 2 (5.1%) and 3 (10.9%) in overall yield of 354 g (83.3%).

Comparative FWA 1 (R=CH3; R1, R3=H; R2, R4=C6H3(SO3Na)2)

74.5 g (0.54 mol) of N-Me taurine are added to the solution from step 2 of Example 1 during 20 minutes. The pH is kept constant at 8 by the simultaneous addition of 10% sodium hydroxide solution while heating the mixture up to 100° C. The reaction mixture is then stirred at about 100° C. and pH 8 for additional 3 hours. The resulting solution is cooled to about 50° C. and clarified by filtration to yield the solution of the compound of formula 1, 383 g (88.7.3%).

The following fluorescent whitening agents and mixtures were obtained, wherein M means always sodium and wherein Standard FWA means Comparative FWA 1. Blankophor UWS as shown below is used in the examples below as Comparative FWA 2 for comparison purposes.

Standard FWA

Blankophor UWS

Example 1

Example 2

(78.7%)

(4.8%)

(16.5%)

Mixtures of mono- and di taurine FWAs

Example 3

(84%)

(5.1%)

(10.9%)

These fluorescent whitening agents and mixtures were used in the following application examples.

Application Example 1

The whitening performance of different fluorescent whitening agents was studied using the following test procedure for size-/film-press application.

A 15% starch solution of neutral potato starch (Perfectamyl 4692) was prepared. The tests were done in a 10% starch solution. The amounts (calculated on dry paper) of fluorescent whitening agent were between 0.1-0.5%, applied on paper. 1.6 g/m2 of dry starch was applied on a 80 g/m2 basepaper, which was a machine paper, sized and slightly whitened with fluorescent whitening agent.

First the fluorescent whitening agent was weighed in a glass, and 13.33 g of starch solution was added. Afterwards the solution was filled up with water to 20 g, so that the tests were done in a 10% starch solution. After stirring for a short time the solution was applied on one side of the basepaper by a semiautomatic lab coater with a Rakel (No. 0), which should simulate a film press application. After the drawing the paper was directly dried on a drying cylinder at about 100° C. After climatization overnight the prepared side of the papers were measured with a Data-color spectrometer (ISO2469) by determining CIE, L*, a* and b*, the light source used based on ISO2469 standard.

The amounts used of fluorescent whitening agent per 100 g starch preparation were between 0.28 and 1.12% as indicated in Table 1.

Figure 1:
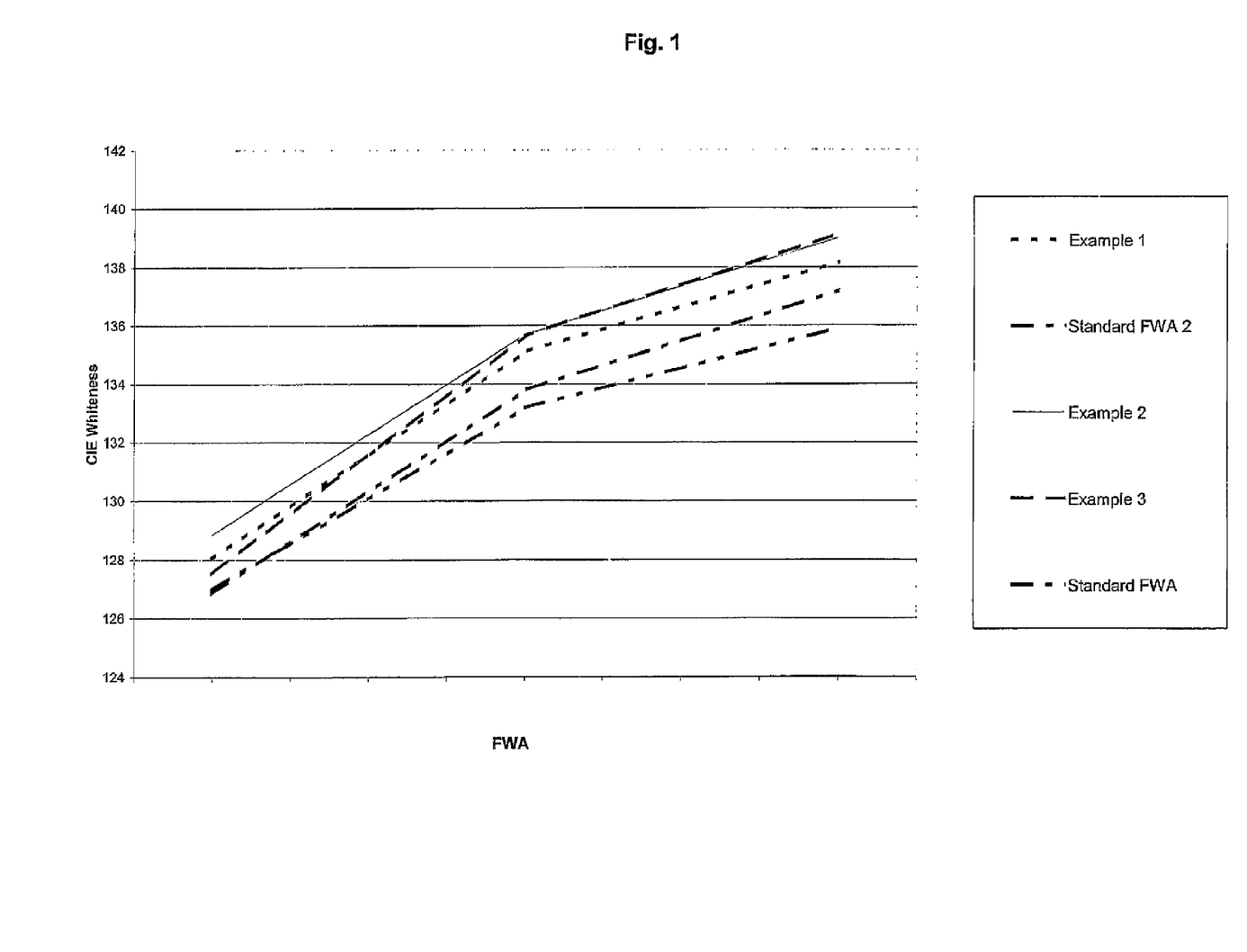
FIG. 1 is a diagram showing the whitening performance of different fluorescent whitening agents (FWAs).

The results obtained are summarized in Table 1 and also shown in FIG. 1.

TABLE 1

| FWA | Amount (wt %) FWA in Starch preparation | CIE whiteness | L* | a* | b* |
|---|---|---|---|---|---|
| Example 1 | 0.28 | 128.05 | 94.10 | 2.30 | −9.38 |
|  | 0.56 | 135.11 | 94.30 | 2.51 | −10.88 |
|  | 0.84 | 138.16 | 94.37 | 2.54 | −11.53 |
|  | 1.12 | 139.47 | 94.43 | 2.43 | −11.79 |
| Example 2 | 0.28 | 128.86 | 94.09 | 2.48 | −9.58 |
|  | 0.56 | 135.69 | 94.30 | 2.71 | −11.01 |
|  | 0.84 | 139.00 | 94.37 | 2.74 | −11.72 |
|  | 1.12 | 141.03 | 94.47 | 2.71 | −12.13 |
| Example 3 | 0.28 | 127.53 | 94.04 | 2.37 | −9.30 |
|  | 0.56 | 135.66 | 94.23 | 2.72 | −11.03 |
|  | 0.84 | 139.13 | 94.39 | 2.75 | −11.74 |
|  | 1.12 | 140.95 | 94.42 | 2.73 | −12.14 |
| Comparative FWA 1 | 0.28 | 126.86 | 94.03 | 2.31 | −9.16 |
|  | 0.56 | 133.79 | 94.22 | 2.56 | −10.62 |
|  | 0.84 | 137.19 | 94.31 | 2.62 | −11.34 |
|  | 1.12 | 139.78 | 94.35 | 2.61 | −11.90 |
| Comparative FWA 2 | 0.28 | 126.99 | 93.99 | 2.19 | −9.20 |
|  | 0.56 | 133.19 | 94.2 | 2.32 | −10.49 |
|  | 0.84 | 135.91 | 94.40 | 2.23 | −11.01 |
|  | 1.12 | 136.80 | 94.48 | 2.05 | −11.17 |

Application Example 2

The whitening performance of different fluorescent whitening agents was studied in the presence of calcium chloride.

The test procedure was the same as in Application Example 1, except that calcium chloride was added as follows. A 50% calcium chloride solution was prepared. The amount of calcium chloride was 0.8%, applied on paper. After weighing the fluorescent whitening agent in a glass and adding 13.33 g of the 15% starch solution, calcium chloride solution was weighed in and the solution was filled up with water to 20 g.

The amounts used of fluorescent whitening agent per 100 g starch preparation were between 0.24 and 0.73% as indicated in Table 2.

Figure 2:
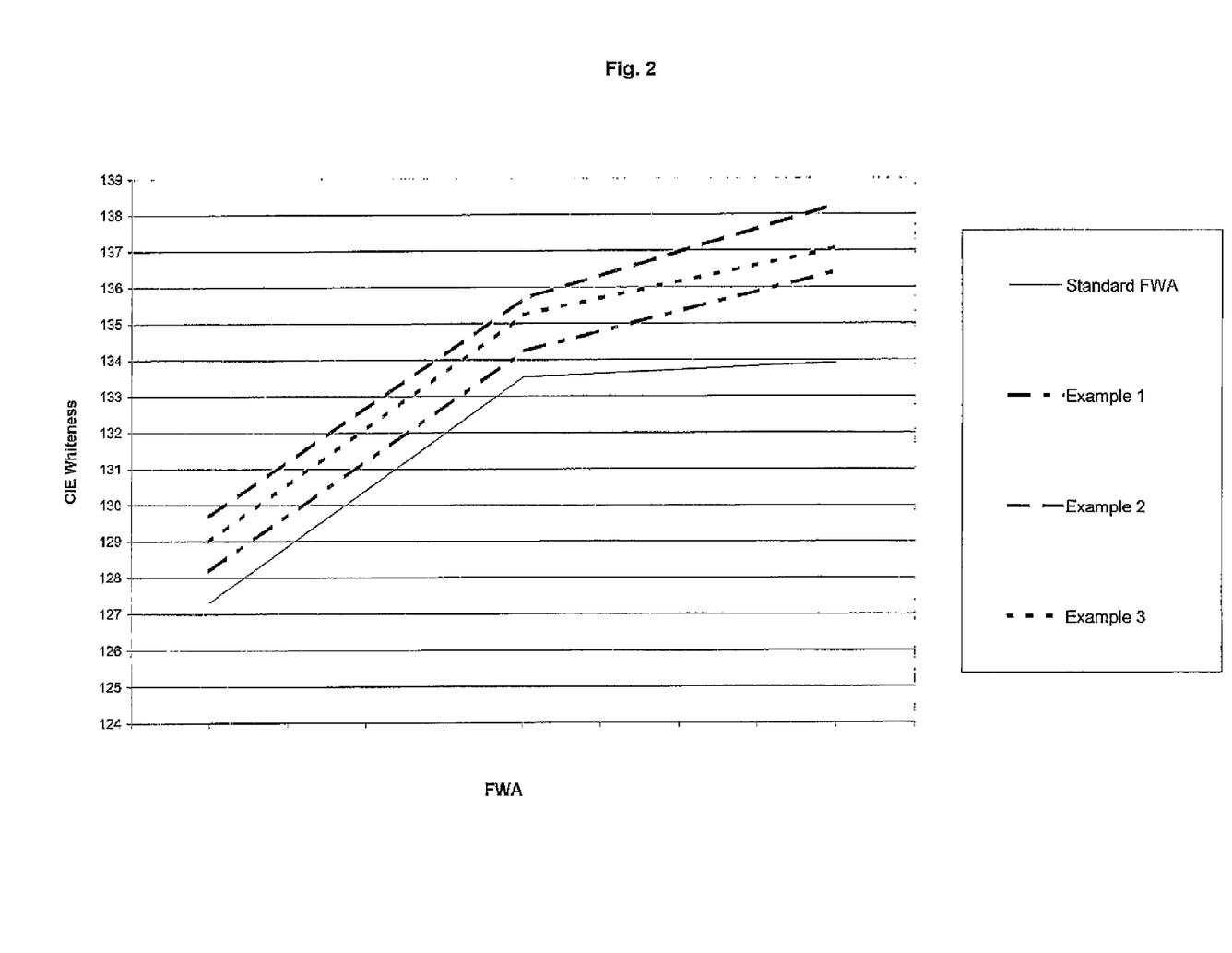
FIG. 2 is a diagram showing the whitening performance of different fluorescent whitening agents (FWAs) in the presence of a salt of a bivalent cation.

The results obtained are summarized in Table 2 and also shown in FIG. 2.

TABLE 2

| FWA | Amount (wt %) FWA in Starch preparation | CIE whiteness | L* | a* | b* |
|---|---|---|---|---|---|
| Example 1 | 0.24 | 128.19 | 93.95 | 2.22 | −9.48 |
|  | 0.49 | 134.24 | 94.18 | 2.28 | −10.73 |
|  | 0.73 | 136.44 | 94.34 | 2.16 | −11.15 |
| Example 2 | 0.24 | 129.69 | 94.01 | 2.17 | −9.34 |
|  | 0.49 | 135.68 | 94.21 | 2.24 | −10.59 |
|  | 0.73 | 138.27 | 94.34 | 2.15 | −11.11 |
| Example 3 | 0.24 | 129.00 | 94.05 | 1.99 | −9.07 |
|  | 0.49 | 135.24 | 94.24 | 2.02 | −10.31 |
|  | 0.73 | 137.08 | 94.32 | 2.01 | −10.91 |
| Comparative FWA 1 | 0.24 | 127.31 | 93.99 | 2.05 | −9.26 |
|  | 0.49 | 133.51 | 94.17 | 2.12 | −10.57 |
|  | 0.73 | 133.93 | 94.33 | 2.03 | −10.59 |

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A composition suitable for paper brightening, wherein the composition comprises:

three fluorescent whitening agents (FWA) represented by formula (1), formula (2) and formula (3):

1

2

3 wherein R represents independently hydrogen, $C_1$-$C_3$ alkyl or $C_1$-$C_3$ hydroxyalkyl; $R_1$, $R_2$, $R_3$ and $R_4$ represent independently of each other, hydrogen, cyano, $C_1$-$C_4$ alkyl, $C_2$-$C_4$ hydroxyalkyl, $C_1$-$C_4$ alkoxy, wherein alkyl is linear or branched; or $R_2$ and $R_1$ or $R_3$ and $R_4$ independently of each other together with N atom form a morpholine ring, a piperidine ring or pyrrolidine ring; or —$(CH_2)_l$—$SO_3M$, where l is 1, 2 or 3; or —$(SO_3M)k$, wherein the —$SO_3M$ groups can be in o-, m-, or p-position and k is an integer from 0 to 3; or —$(CH_2)_i$—COOR, —$(CH_2)_i$—CONHR, —$(CH_2)_i$—COR, where i is an integer from 1 to 4, R is $C_1$-$C_3$ alkyl or equals to M; and M represents hydrogen, or one equivalent of a cation selected from the group consisting of Li, Na, K, Ca, Mg, and ammonium, wherein the ammonium cation is unsubstituted or mono- di-, tri- or tetra-substituted by $C_1$-$C_4$ alkyl or $C_2$-$C_4$ hydroxyalkyl; and wherein the composition contains the fluorescent whitening agent of formula (1) in an amount of 50 to 90 weight-%, the fluorescent whitening agent of formula (2) in an amount of 1 to 20 weight-% and the fluorescent whitening agent of formula (3) in an amount of 1 to 30 weight-%, wherein the weight-% is based on a total amount of the fluorescent whitening agents.

2. The composition of claim 1, wherein R, $R_1$ and $R_3$ are hydrogen, and $R_2$ and $R_4$ are 2,5-disulfophenyl.

3. The composition of claim 1, wherein R is methyl, R1 and R3 are hydrogen, and R2 and R4 are 2,5-disulfophenyl.

4. The composition of claim 1, wherein M is Na or K.

5. The composition of claim 1, wherein the composition is an aqueous preparation.

6. The composition of claim 1, wherein the composition is a size press liquor.

7. The composition of claim 1, wherein the composition is a coating composition or coating slip.

8. The composition of claim 1, wherein the composition contains a salt of a bivalent cation.

9. A process for whitening paper, comprising contacting a pulp or pulp suspension with the composition of claim 1.

10. A process for whitening paper, comprising contacting a cellulose sheet with the composition of claim 1.

11. The process of claim 10, wherein the contacting with the cellulose sheet is conducted in a size press or by coating.

12. A paper obtainable by the process of claim 9.

13. A paper obtainable by the process of claim 10.

* * * * *